(12) United States Patent
Blechschmidt et al.

(10) Patent No.: US 9,381,458 B2
(45) Date of Patent: Jul. 5, 2016

(54) DEVICE FOR DISINFECTING GASES AND/OR LIQUIDS

(75) Inventors: Jörg Blechschmidt, Zornheim (DE); Reiner Bartsch, Tirschenreuth (DE)

(73) Assignee: Schott AG, Mainz (DE)

( * ) Notice: Subject to any disclaimer, the term of this patent is extended or adjusted under 35 U.S.C. 154(b) by 624 days.

(21) Appl. No.: 13/606,344

(22) Filed: Sep. 7, 2012

(65) Prior Publication Data

US 2013/0236353 A1     Sep. 12, 2013

(30) Foreign Application Priority Data

Sep. 8, 2011   (DE) .......................... 10 2011 112 994
Aug. 16, 2012  (EP) ..................................... 12005891

(51) Int. Cl.
| | |
|---|---|
| B01D 53/00 | (2006.01) |
| A61L 2/10 | (2006.01) |
| A61L 9/20 | (2006.01) |
| C02F 1/32 | (2006.01) |

(52) U.S. Cl.
CPC ................ B01D 53/007 (2013.01); A61L 2/10 (2013.01); A61L 9/20 (2013.01); C02F 1/32 (2013.01); C02F 1/325 (2013.01); *C02F 2201/3222* (2013.01); *C02F 2201/3227* (2013.01); *C02F 2201/3228* (2013.01); *C02F 2303/04* (2013.01)

(58) Field of Classification Search
USPC .............. 250/432 R, 435; 422/4; 210/748.11, 210/198.1, 418; 92/224
See application file for complete search history.

(56) References Cited

U.S. PATENT DOCUMENTS

| | | | |
|---|---|---|---|
| 3,994,708 A | 11/1976 | von Reth et al. | |
| 5,133,932 A | 7/1992 | Gunn et al. | |
| 7,270,748 B1 | 9/2007 | Lieggi | |
| 2003/0170151 A1 | 9/2003 | Hunter et al. | |
| 2005/0000913 A1* | 1/2005 | Betterly ................. | C02F 1/325 210/748.11 |
| 2008/0259602 A1* | 10/2008 | Fechner ................. | C03C 3/076 362/247 |
| 2010/0237254 A1* | 9/2010 | Mason ..................... | A61L 2/10 250/435 |
| 2010/0253207 A1 | 10/2010 | Joulaud et al. | |
| 2012/0051977 A1* | 3/2012 | Boodaghians .......... | C02F 1/325 422/117 |

FOREIGN PATENT DOCUMENTS

| | | |
|---|---|---|
| CN | 1103384 A | 6/1995 |
| CN | 2618604 Y | 6/2004 |
| DE | 38 24 647 A1 | 2/1990 |
| DE | 38 37 905 A1 | 5/1990 |
| DE | 196 17 467 A1 | 11/1997 |
| DE | 10 2004 018 148 A1 | 11/2005 |
| DE | 10 2007 013 191 A1 | 9/2008 |
| DE | 10 2010 005 893 A1 | 7/2011 |
| EP | 1 726 573 A1 | 11/2006 |

(Continued)

*Primary Examiner* — Phillip A Johnston
*Assistant Examiner* — Hsien Tai
(74) *Attorney, Agent, or Firm* — Taylor IP, P.C.

(57) ABSTRACT

A device for disinfecting of gases and/or liquids, includes a tube of UV-transparent glass having a hollow interior space and a tube wall with a tube inside wall and a tube outside wall, as well as at least one UV-light source. The UV-transparent glass tube has an indentation extending into the interior space on at least one location and in the at least one indentation at least one UV-light source is arranged. The geometry causes the UV-light sources to be closer to the medium to be disinfected, so that a large portion of the UV-light reaches the interior space on a direct path through the glass, thus allowing for a low-loss transfer of the UV-light.

28 Claims, 7 Drawing Sheets

(56) References Cited

FOREIGN PATENT DOCUMENTS

| | | |
|---|---|---|
| JP | 1-299693 A | 12/1989 |
| JP | 2001-293469 A | 10/2001 |
| JP | 2011-32162 A | 2/2011 |
| WO | 2009/013507 A1 | 1/2009 |

\* cited by examiner

DEVICE FOR DISINFECTING GASES AND/OR LIQUIDS

BACKGROUND OF THE INVENTION

1. Field of the Invention

The present invention relates to a device for disinfecting of gases and/or liquids.

2. Description of the Related Art

An already known method is to utilize ultraviolet (UV) radiation for treatment, in particular disinfecting or respectively sterilizing water, air or surfaces. Drinking water treatment by means of UV-radiation has hitherto been relatively common, whereby the germination index in the water can be greatly reduced reliably and dependent upon the dose. UV-radiation inactivates micro-organisms such as pathogens, in particular bacteria or viruses.

UV-disinfection offers a series of advantages compared to conventional disinfection, based on chemical processes. UV-disinfection is a simple and rapidly effective process whereby disinfection occurs immediately during the exposure of the medium. Another great advantage of UV-disinfection is that neither taste, odor, nor pH-value of the disinfected medium is influenced. This represents a substantial difference from the chemical treatment of drinking or process water. In contrast to the chemical disinfection process additional disinfection agents are not required. Maintenance and monitoring of dosing equipment are not required and special safety regulations are also not necessary. An additional advantage is that it is environmentally friendly since no secondary reactions due to formation of undesired compounds occur. In contrast to conventional disinfection agents no resistance due to mutation, as is often the case for example with hospital specific germs (for example antibiotic-resistance), are developed in UV-disinfection. UV-disinfection is also possible in a large scale, for example in communal drinking water processing. It is also possible in continuous operation to keep the germination index constantly low.

In UV-disinfection, mercury vapor lamps which emit radiation at a wavelength of around 254 nanometers (nm) are normally utilized. Shorter wavelengths below 200 nm are so short-wave that they are absorbed by molecular oxygen, whereby the molecular oxygen is split into free oxygen radicals and can further react with additional oxygen molecules to create ozone. Short wave UV-radiation of this type is also utilized to produce ultrapure water.

Numerous suggestions for UV-disinfection are known from the current state of the art. Some of these are discussed hereafter. For example, DE 38 37 905 A1 describes a method and a device for the treatment, in particular disinfection of liquids and/or gases by means of UV-light sources, whereby the device is a tubular reaction chamber for the medium which is to be treated and comprises at least two UV-light sources, whereby light sources differing from each other are provided which respectively emit different wave lengths and which jointly can be operated in selectable combinations together or, alternatively, separately. The UV-light sources are located either in the reaction chamber and are immersed into the medium and are surrounded by same, or are positioned outside and at a distance from the reaction chamber.

DE 38 24 647 A1 relates to a device to radiate mediums by means of UV-light, consisting of a tubular body of UV-permeable material through which medium flows, and at least two UV-light sources with reflectors mounted externally axially parallel whereby the light sources represent UV flat emitters having an elongated, flat oval cross section with a broadside and a narrow side. The main axis of the UV-light sources are always directed to the center point of the tubular body cross section. The UV-light sources are arranged ring-shaped and axially parallel around the tubular body through which the medium flows. According to one embodiment, the flat emitters fit against the tubular body with the narrow side facing the tubular body.

U.S. Pat. No. 5,133,932 discloses a device to sterilize blood and other liquids of biological origin, whereby a container which is transparent regarding UV-radiation is rotated with the liquid to be sterilized and is simultaneously radiated from the outside with UV-radiation. The container may possess a wave-like surface. The UV-light sources are however located outside the rotatable container.

DE 196 17 467 A1 furthermore concerns a device for disinfecting of water by means of UV-C-rays, whereby the water flows through a quartz glass tube and whereby one or several UV radiators are positioned around the quartz glass tube.

DE 10 2010 005 893 A1 discloses a line for the production of ultrapure water, comprising at least one inlet for the water to be purified, a purification unit, a UV-radiation unit with at least one UV-ray emitting light source which is designed for radiating the water flowing through the UV-radiation unit, as well as one outlet. The UV-radiation units, for example in the embodiment of UV-LEDs (light emitting diodes), are arranged either externally of the conduit system 14 (FIG. 6d) or are integrated into the walls of conduit system 14 (FIGS. 6a, 6b and 6c). It is particularly preferred if the UV-radiation unit protrudes at least partially into the flowing water.

WO 2009/013507 relates to a treatment device for at least partial disinfection of a fluid such as water, comprising one conduit for conveying a flow of fluid to be treated, a multitude of LEDs for the emission of UV-light into the fluid, as well as a control circuit for controlling the LEDs by means of a pulsed signal for pulsing the light source. Herein the UV-LEDs are arranged such that the fluid flows directly over a surface of each light source. The direct contact of the fluid with the UV-source/sources is intended to provide greater treatment efficiency due to the closer proximity of the light source to the fluid to be treated. Furthermore, a cooling effect provided by the UV-LEDs allows operation of the LED at highest UV-light intensity, thereby increasing fields of application and efficiency.

A problem in the direct contact of UV-light source and medium to be treated is in that the surface of the UV-light source must be resistant against the medium and must be sealed against same. Each UV-LED must be individually sealed. The cooling effect, for example that of a liquid, can no longer be utilized if the liquid itself is not cool, but is instead warm or even hot. In such a case the hot liquid causes even additional heating of the UV-LEDs and can thereby clearly limit their life span.

The described treatment systems also have the disadvantage here that no simple replacement of the UV-light source can occur, since this is in direct contact with the medium to be treated. Shutting down the entire system is therefore required, thereby reducing the efficiency of the method.

U.S. Pat. No. 7,270,748 B1 describes a water purification system for a water faucet by use of UV-radiation. Part of the water flow is equipped with a multitude of UV-LEDs which can be arranged around the transparent conduit and may be embedded in same.

U.S. Patent Application Publication No. 2003/0170151 A1 discloses a system wherein a fluid is subjected to UV-radiation. The system includes a conduit for conveying the fluid, whereby the conduit is baffled so that the fluid flow is rendered more uniform. The UV-light sources are hereby arranged in the conduit or can also be provided on the baffle unit. The UV-light sources are hereby again in direct contact with the fluid to be treated, resulting in the already described disadvantages.

U.S. Patent Application Publication No. 2010/0253207 A1 describes a flat discharge lamp of a very special design to produce UV-radiation which, in addition to other applications, can also be used to disinfect/sterilize air, water or surfaces.

Accordingly, two essentially different design concepts for UV-disinfection units are known from the current state of the art:

a) units wherein the UV-light sources are surrounded by the medium to be disinfected; and
b) units wherein the UV-light sources are arranged outside the medium to be disinfected.

Disadvantages of known systems of type (b) are low efficiency and large space requirement. With these systems the UV-light sources are arranged outside a UV-permeable tube, through which the medium to be disinfected flows. In order to guarantee the minimum radiation necessary for radiation in the interior space which is completely filled with flowing medium, a multitude of UV-light sources must either be arranged around the tube, or the UV-radiation of fewer light sources must be distributed to a sufficient extent over an expensive reflector system which requires a comparatively large space. In order to achieve sufficient disinfection performance two criteria must be met: the radiation intensity must be sufficiently high over the entire range to be disinfected, which means that the intensity of the radiation for disinfection should not fall below a certain radiation minimum. Moreover, a distribution of radiation which is as homogeneous as possible should be present in the medium to be disinfected. Systems known from the current state of the art however, typically have the problem of poor utilization of UV light, caused by shading, multiple reflections and loss mechanisms, in particular on the reflective surfaces of the reflector system. Due to the generally undirected radiation of the UV-light sources, only a small portion of the radiation takes a direct path through the UV-permeable tube into the medium to be disinfected. The remaining portion must be directed into the tube via reflectors. Reflector materials, such as aluminum however absorb a significant portion of the UV-radiation. In the case of aluminum, this absorption is approximately 15% at a wavelength of 254 nm. This portion of UV-radiation is lost and is no longer available to disinfect.

Moreover, the known arrangements of UV-light sources and reflectors require a lot of space and are therefore suitable only to a limited extent for applications requiring a small space.

What is needed in the art is a device wherein the disadvantages of the current state of the art are avoided and which provides an effective disinfection of liquids or gases using UV-radiation while maintaining the known advantages of a UV-disinfection, whereby better utilization of the UV-radiation produced by the light sources is achieved. Moreover the inventive device is to provide high compactness in regard to its construction.

SUMMARY OF THE INVENTION

According to the present invention, there is provided a device for disinfecting of gases and/or liquids, including a tube of UV-transparent glass having a hollow interior space and a tube wall with a tube inside wall and a tube outside wall, as well as at least one UV-light source. The UV-transparent glass tube has an indentation extending into the interior space on at least one location and in the at least one indentation at least one UV-light source is arranged.

The geometry of the current invention is therefore based on a placement of at least one UV-light source which is surrounded at least partially by the glass wall of the tube and is located inside same. The glass wall is thereby shaped in such a way that the glass wall can accommodate the UV-light source at least partially, for example completely. Therefore, indentations are provided in the glass tube wall in order to provide the one or multiple UV-light sources. Therefore there is a clear spatial separation of the UV-light source and the medium to be treated—the gas to be disinfected and/or the liquid to be disinfected is not in direct contact with the UV-light source.

Within the scope of the current invention an "indentation" represents an inversion of a predetermined size in the glass wall of the glass tube in which at least one UV-light source is arranged. The inside tube wall and the outside tube wall are hereby inverted simultaneously toward the inside at the same location and together form a hollow space which is open toward the outside of the tube and in which the at least one UV-light source is accommodated. The hollow space formed by the indentation is open toward the outside of the tube in order to facilitate access to the UV-light source. The UV-light source can herewith easily be connected to, and disconnected from the electric connections so that the UV-light sources can easily be replaced. The inventive indentations therefore extend at least partially into the inside space of the glass tube.

According to the current invention recesses may also be present in the glass tube. According to the invention a "recess" is a depression of a predetermined size which is provided either in the outside tube wall or the inside tube wall of the glass tube. For the provision of a recess, material is removed. If, for example, one or several recesses are provided in the inside tube wall, material is removed for this purpose in order to form the recesses. The outside tube wall however remains unaffected by this. If, for example, one or several recesses are provided in the outside tube wall, material is removed for this purpose in order to form the recesses. The inside tube wall however remains unaffected by this. In contrast to the inventively provided indentations, these recesses do not extend into the inner space of the glass tube which remains unaffected by the provision of recesses.

The recesses which may possibly be provided in addition to the inventive indentations may accommodate one or more UV-light sources. However, the optional recesses may serve other functions and not contain any UV-light sources. The recesses may, for example, contain a sensor or other technical devices which may be utilized for the device of the present invention. According to an additional embodiment of the present invention, the glass tube may be provided with only indentations. Recesses are then not present.

According to the present invention, the number of UV-light sources used may be selected relatively discretionary. At least one UV-light source is provided. Also, at least 2 UV-light sources may be present. Exemplary embodiments of the present invention include 1 to 8 UV-light sources, for example 1 to 6 UV-light sources, or 1 to 5 UV-light sources. Potentially, there may, for example, be 1 to 4 or 1 to 3 UV-light sources in the glass tube. If relatively strongly radiating UV-light sources, such as conventional UV-bar lights, are used it is possible due to cost considerations to use as few as possible UV-light sources, for example 1 to a maximum of 3 UV-lamps. If relatively weakly radiating UV-lamps are used, such as UV-LEDs then a clearly greater number of UV-light sources can be used according to the present invention, for example 100 UV-LEDs or more. In each case radiation intensity should not fall below a predetermined minimum. There should be an as uniform as possible distribution of the UV-light, in order to guarantee sufficient disinfection.

Depending on the selected number, the arrangement of the UV-light sources occurs such that an as uniform as possible distribution of the light sources may be present across the entire tube circumference. Symmetric arrangements may this be utilized, for example axially symmetric or mirror symmetric, rotationally symmetric or centrically symmetric arrangements. With a non-symmetric arrangement of the UV-light sources areas can result in the medium to be disinfected which are clearly reached by less UV-light. This should be avoided. In providing three UV-light sources the UV-light sources may be arranged so that they form an equilateral triangle (imagined connecting lines between the individual UV-light sources as the corners to represent an equilateral triangle). With four UV-light sources they may be arranged on the corners of an imagined square. With five UV-light sources they may be located on the corners of a pentagon having uniformly long sides, etc.

In addition to the number, size and design of UV-light sources the selection of a suitable arrangement of UV-light sources also depends on the selected configuration, size and cross section of the glass tube. An expert from the current state of the art can easily select a suitable, for example an as symmetric as possible, arrangement of UV-light sources for each type of tube.

The number of indentations may coincide with the number of the utilized UV-light sources. In individual instances however, there may be more indentations than UV-light sources, or several UV-light sources may also be present in one indentation.

It is furthermore possible that only one UV-light source is provided in one indentation. This leads to a more favorable exploitation of the UV-radiation while avoiding mutual shadowing of the UV-light sources. In contrast, several, possibly even a large number of UV-light sources are arranged in one indentation when using UV-LEDs. The reason is that LEDs radiate directionally, thereby being able to avoid mutual shadowing.

The inventive arrangement offers advantages especially when using tube materials which are not completely UV-transparent, in particular when using the introduced UV-transparent glasses. Since glass tubes of UV-transparent glasses can have an absorption of >10% on 1 millimeter (mm) material thickness at a wavelength of 254 nm, in the case of the inventive device the light may only pass a short distance through the glass and not be already absorbed to a high degree in the tube material.

The term "UV-transparent" means that the inventively utilized tube glass possesses high UV-transmission, meaning it has a UV-transmission of at least 75% at a wavelength of 254 nm and a layer thickness of the glass of 1 nm. According to an embodiment of the present invention the tube glass has a transmission at a layer thickness of 1 mm in the UV-range which is at 200 nm<0.5% and at 254 nm>75%. A transmission at a layer thickness of 1 mm in the UV-range at 200 nm<0.3% and at 254 nm>80% is also possible.

The inventive solution of providing the UV-light sources in the indentations is characterized in that the UV-light sources are offset in the direction toward the interior space of the tube. The result is a high portion of UV-radiation which is led directly through the glass tube into the medium without incurring prior reflective losses. Thanks to the geometry provided by the present invention a more homogeneous light distribution in the interior space of the tube is furthermore achieved, thereby increasing the disinfection efficiency. Moreover, a highly compact system is made available by the arrangement according to the present invention.

With the device according to the present invention therefore, more UV-radiation reaches the medium than with a conventional arrangement where the UV-light sources are located outside the tube containing the medium to be disinfected. In contrast to the previously described systems according to type (a) which as a rule are based on a very complex system design, the inventive device is configured to be relatively simply. In particular in systems of type (a) the UV-light source must be accessible from the outside which represents additional engineering effort which in turn is again connected with high expenditure. In contrast, the inventive device permits easy access to the UV-light source so that replacement of same is simple. Based on the simple system configuration according to the present invention an almost uninterrupted flow of medium through the glass tube can occur.

According to a further embodiment of the present invention, the shape of the indentations may be adapted to the shape of the used UV-light sources. The indentations are appropriately shaped such that they can accommodate this UV-light source at least partially, for example completely. The special shape of the indentation which is adapted to the light source serves to optimize the light distribution, so that all zones inside the conduit receive sufficient radiation strength. This plays a role particularly at the inner conduit edge, centered between individual light sources, where otherwise only low radiation intensity would be present.

According to a further embodiment of the present invention, the at least one UV-light source is arranged in the at least one indentation such that the at least one UV-light source is located at least partially, for example completely, within the inside tube wall of the UV-transparent glass tube, if the inside tube wall were not provided with indentations. In this instance "inside tube wall" is to be understood to be the inside of the tube as it would appear without indentations, in other words if there were no indentations in the glass tube.

According to another embodiment of the present invention wherein the glass tube has a round cross section, the indentations may reach into the interior space of the glass tube to the extent that the UV-light sources contained therein are located at least partially, for example completely inside the inside radius of the tube. "Tube inside radius" is to be understood as being the inside of the tube, as it would be without indentations, in other words if no indentations were present in the glass tube.

With this geometry according to the present invention, a majority of the radiation (at least 180° angle of reflection) can reach on a direct path through the glass wall into the interior space and does not get lost through back reflections into the light sources and/or through other absorption, for example at the reflector. Such arrangements include a configuration wherein the UV-light sources are arranged so that they are located inside the tube inside wall, as previously defined, so that an especially favorable radiation distribution results whereby the predominant portion of the UV-light is directed on a direct path through the glass into the interior space. In comparison to conventional arrangements therefore, the present invention succeeds in that only a small radiation portion is reflected back through reflectors. The result is a higher overall efficiency of the system.

According to the present invention the indentations are may be locally limited in the glass tube, in other words, the indentation may have a predefined shape and size; they may be present only in the zone of a UV-light source or a group of UV-light sources and not extend further along the tube axis.

However, it may also be advantageous—for example due to production technical reasons—to provide an indentation which is larger than the therein contained UV-light source. The indentations may for example also be provided circumferentially around the tube.

For example, only one UV-light source or one group of UV-light sources at a time may be provided in one indentation. If, according to the present invention, only indentations are provided in the glass tube, this can be especially expedient for the production process; this will yet be described in further detail.

An additional embodiment of the inventive device is a reflector which is arranged outside the tube in order to reflect the UV-light which was radiated to the outside again back into the tube. Through targeted reflector geometry the reflectors also serve to reduce the portion of the UV-radiation which is reflected back into the light source to a minimum, or respectively to reflect UV-light emerging from the medium, in particular on the opposite side, back into the medium.

The type, shape, size and structure of the reflector are not restricted inventively. A reflector may be any type of component, including a surface for the purpose of reflecting light. The reflector may be constructed in various variations. The reflector may, for example, be constructed of flexible or rigid or respectively solid material. The reflector may be of a shape and size which conforms to the shape and size of the inventive device, in particular the UV-transparent glass tube with at least one UV-light source.

The reflector may for example be advantageously arranged around the glass, enveloping same completely, meaning that the reactor is arranged around the entire inventive device. In this case the reflector may assume the embodiment of a tube, for example a tube of aluminum, stainless steel or another material. It can possibly be provided with an appropriately reflective coating and have a larger diameter than the glass tube whose circumference is completely enclosed by the reflector. The shape and the cross section of the reflector tube can hereby be similar in shape or cross section to the glass tube. The reflector tube can at the same time serve as protection for the glass tube.

According to an additional embodiment of the present invention, a reflector is positioned immediately on the glass tube, whereby possibly no reflector is provided in the area of the indentations. The reflector may for example be attached on the outside wall of the tube—with the exception of the area where the indentations and, if applicable, the recesses are located—for example in the form of a UV-reflective coating on the outside wall of the tube.

According to another embodiment of the present invention the reflector may also be positioned on the inside of the glass tube, whereby for example a UV-reflective coating is provided on the inside wall of the tube. Here, the indentations for the UV-light sources are again recessed. In this case the reflected light is not weakened by the residual absorption of the glass.

The reflector can also consist of several different components, for example of individual reflectors which are located, for example behind the UV-light sources. One reflector may then be allocated to each UV-light source or to a group of UV-light sources, in order to provide an as high as possible radiation energy for the radiation of the medium flowing in the tube. In configuration design and shape, the individual reflectors allocated to the respective UV-light sources are approximated to the shape of a conical section, for example parabolic or elliptical.

There can also be a combination of different reflectors. One reflector may be provided on the outside or the inside of the glass tube and also one reflector is additionally provided on each UV-light source. For example, one reflector can be separately arranged on the glass tube, outside or inside or immediately on the glass tube, with the exception of the areas of the indentations, where an additional reflector may be provided for each UV-light source. According to a further embodiment of the present invention, a UV-reflecting coating is provided for example on the outside wall of the tube or the inside wall of the tube of the inventive device. In the area where the indentations, and possibly the recesses, are located and were the radiation is to reach into the interior space there is no coating since the surface here is interrupted so that separate reflectors may be provided respectively. A simple reflector geometry is therefore possible in the inventive device, whereby the reflector may be arranged separately from the glass tube—outside or inside—or on the glass tube while omitting the UV-light sources.

The shape and size or the cross section of the glass tube is also not strictly limited according to the present invention. The cross section may be selected as desired, as long as the constructive constraints for the intended application permit. The cross section of the tube is, for example, selected to be round, oval, angular, for example having 3, 4, 5, 6, 7 or 8 corners. The cross section of the tube may, for example, represent a pentagonal base contour with indentations for the lamps on the five corners or the cross section of the tube, can have an elliptic base contour with indentations on the more pointed curvatures, or the cross section of the tube may be round with, for example, a uniform distribution of UV-light sources around the entire tube circumference.

According to the present invention a round tube or a tube which has a fundamentally round base contour may be utilized. If indentations in the glass wall in a tube having a round base contour are present, then the inside wall of the tube can have a round inside contour and the outside wall of the tube can also have a round outside contour which is interrupted only by the present indentations.

According to the present invention a fundamentally round base contour is to be broadly understood whereby the cross section of a tube can, for example, also have a star-like or wave-like configuration derived from the round basic shape which is still present if one disregards the additional structures. The tube cross section can also display a precise round outer and inner contour, in other words with a predefined inside and outside radius.

According to the present invention, the indentations can be of any desired shape and size. They may, for example, be pointed and/or rounded. Round or rounded shapes which are adapted to the shape of the UV-light source may be utilized for the indentations. Moreover, such shapes may also be utilized which facilitate targeted directing of the UV-light into the interior space of the glass tube. For example, all indentations in the glass tube may be the same shape and size.

The inventively utilized UV-light sources are also not particularly limited within the scope of the invention. Any type of known UV-light source may be used, whereby normally UV-radiation at a wave length of 253.7 nm is used. This represents the main emission wave length of low-pressure UV-lamps and a fundamental radiation maximum of other UV-lamps. Medium pressure, high pressure or low pressure UV-lamps are therefore used, for example mercury vapor medium pressure-, high pressure- or low pressure lamps which emit radiation at a wave length of around 254 nm. Low pressure UV-lamps, such as low pressure mercury vapor lamps may be used. According to another embodiment of the present invention, UV-light sources in the form of CCLs (cold cathode lamps) may be used. These are based on the proven CCFLtechnology (cold cathode fluorescent lamp) whereby the fluorescent coating is waived and which can currently already be obtained on the open market. According to the present invention UV-LEDs can also be used. If UV-LEDs are used, a higher wavelength in the range of 270 nm may be selected, wherein on the one hand the disinfecting effect is greater. On the other hand, typical UV-transparent glasses have a higher transmission at these wavelengths which increases the efficiency further.

Generally the tubes distinguish themselves in that their tube walls have a certain shape in the form of a contour, which extends at a certain length in the direction of the longitudinal axis of the tube. In the current invention the contour (profile) is determined by indentations which respectively, for example, progress essentially parallel to the tube axis. A contour may be provided on the outside of a tube as a so-called outer contour and/or on the inside of a tube as a so-called inner contour. The inner- and outer contours can be combined and coordinated so that the wall thickness of the tube around the tube circumference is constant or varied.

If one or more indentations are provided in the tube wall, the wall thickness of the tube may be, in accordance with the present invention, constant along the tube circumference. With an inventive indentation the outer contour conforms to the inner contour; the outer contour always has an indentation if the inner contour is provided with an indentation. The inner and outer contour can also be combined and coordinated with each other so that the wall thickness of the tube is varied along the tube circumference.

The contour can generally have a uniform shape or an irregular shape. Based on the potentially symmetric arrangement of the UV-light sources a uniform shape may be utilized. The indentation can, for example, be wave-like or can have a rounded, rectangular of serrated shape. Combinations of different shapes are possible.

The indentations and, if applicable, the recesses in a glass tube of any desired shape provided in accordance with the current invention can be readily produced according to the knowledge of an expert in the field of glass technology. This is known as so-called contouring or also profiling of the outside and/or inside of a glass conduit.

Contours in the form of indentations, and if applicable recesses, can be created during the glass production process. In potentially utilized method, the contours are introduced into the glass tube directly in a hot forming process. The introduction of contours or profiles into a glass tube is described in DE 10 2004 018 148 A1 (Conturax®-Technology), the disclosure content of which is incorporated into the present application in its entirety.

In the process known from DE 10 2004 018 148 A1 a continuous tube drawing process is used in order to produce calibrated round or profiled glass tubes with a predefined inside profile and a predefined outside profile. During the drawing process the molten glass is hereby drawn over a special profile shaping body. The method can, for example, be used for the known down-draw or Vello-method and the Danner-method.

In continuous tube drawing processes parameters like interior pressure, glass throughput, drawing speed and dimensions of the forming tools are crucial in addition to the viscosity of the glass, whereby all parameters are accordingly coordinated with each other. Tube diameter and wall thickness can be selected independently of each other. The drawing speed for a predefined tube dimension (outside diameter and wall thickness) is hereby correlated with the glass throughput based on the continuity equation.

In the production of glass tubes according to DE 10 2004 018 148 A1 the provision of a larger recess in the outside contour of the glass tube can also lead to a change of the inside contour in an appropriate process, so that an indentation is achieved. In appropriate application of the Conturax®-method, indentations and, if applicable, also recesses can be produced in a glass tube.

With the Conturax®-technology a glass tube having the required indentations can hereby be drawn directly and therefore cost effectively from the melt. The Conturax®-technology can however not be used for quartz glass so that other methods have to be employed.

A glass tube can also be provided with appropriate contours, in particular with indentations, through appropriate refinishing. Contours may for example be introduced through hot pressing and/or rolling into the glass surface.

According to the present invention, the wall thickness of the glass tube may initially be selected at random. Restrictions apply only in regard to the desired application purpose, the desired shape and size as well as to the desired mechanical stability requirements. For example, in domestic use there are connection pressures of approximately 4 to 6 bar which, however, can clearly drop off for example to <1 bar in further progression, for example during discharge from a faucet. In large scale water treatment the pressures are considerably higher, so that the glass tube—depending on the particular application and application location—must be designed for certain pressures. This however represents the know-how of the expert who can easily select the suitable wall thickness for a glass tube for the particular field of application. The expert from the current state of the art also knows how glass tubes of this type can be produced.

Within the scope of the current invention the UV-transparent glass which can be used is also not particularly limited. Any UV-transparent glass known to the expert can be used. For example, UV-transparent glasses which may be used include quartz glasses, silicate glasses, such as borosilicate glasses or sodium-potassium-barium-silicate glasses.

In addition to the desired high UV-permeability of the inventively used glasses, consideration is to be given that they offer sufficient stability vis-à-vis the medium to be disinfected. If, for example water is to be disinfected, a hydrolytically sufficiently stable glass may be used. According to DIN ISO 719 glasses are categorized into 5 water resistant categories. If water is to be disinfected a UV-transparent glass is therefore utilized which, depending on the selected composition has a hydrolytic resistance in category 1 through 3 according to ISO 719 (also referred to as water resistance category or WBK), or has a hydrolytic resistance in category 1 according to ISO 719.

Potential UV-transparent glasses utilized according to the present invention possess one of the following glass compositions (in weight-% on oxide base):

Glass Composition 1:

| | | |
|---|---|---|
| $SiO_2$ | 75-85 | weight-% |
| $B_2O_3$ | 8-15 | weight-% |
| $Al_2O_3$ | 0.5-4 | weight-% |
| $Na_2O$ | 1-6 | weight-% |
| $K_2O$ | 0.1-2 | weight-% |
| $ZrO_2$ | <0.005 | weight-% | with a content $Fe_2O_3$<100 ppm, for example <10 parts per million (ppm),
a content of $TiO_2$<100 ppm, for example <10 ppm
and a content of fining agent.

Alternatively, Glass composition 2 may include:

| | | |
|---|---|---|
| $SiO_2$ | 65-75 | weight-% |
| $B_2O_3$ | 15-22 | weight-% |
| $Al_2O_3$ | 4.5-7 | weight-% |
| $Na_2O$ | 1.5-4 | weight-% |
| $K_2O$ | 0.5-3 | weight-% |
| $Li_2O$ | 0.1-1.5 | weight-% |
| BaO | 0.5-4 | weight-% |
| CaO | 0.1-2 | weight-% |
| MgO | <0.01 | weight-% | with a content $Fe_2O_3$<100 ppm, for example <10 ppm,
a content of $TiO_2$<100 ppm, for example <10 ppm
and a content of fining agent.

A further Glass composition 3 may include, for example:

| | | |
|---|---|---|
| $SiO_2$ | 65-78 | weight-% |
| $B_2O_3$ | 0.5-4 | weight-% |
| $Al_2O_3$ | 0.5-4 | weight-% |
| $Na_2O$ | 5-10 | weight-% |
| $K_2O$ | 8-14 | weight-% |
| BaO | 5-8 | weight-% | with a content $Fe_2O_3$<100 ppm, for example <10 ppm,
a content of $TiO_2$<100 ppm, for example <10 ppm
a content of CaO<100 ppm, for example <10 ppm,
a content of MgO<100 ppm, for example <10 ppm
and a content of fining agent.

Glass 1 for example, may be utilized for disinfecting of water, since it has a hydrolytic resistance in category 1. Glasses 2 and 3 find use, for example, in disinfecting of gases.

Also, the medium to be disinfected is not especially restricted. Any liquid or any gas, or also mixtures of several liquids or gases can be treated in the device according to the present invention. For example, the medium may be water. If aggressive gases or liquids are to be disinfected then, an appropriate selection of suitable glass composition may be made.

The current invention also provides a method of use of the device according to the present invention for disinfecting of liquids and/or gases in stationary or flowing condition, such as in drinking water treatment and disinfection, disinfecting ultrapure water, waste water, liquids from the pharmaceutical and food field, disinfecting of gases such as air or industrial gases and similar as well as in the production of ultrapure water.

The advantages of the invention are exceptionally complex. For the first time the present invention is hereby providing a UV-transparent tube, equipped with at least one indentation, together with at least one UV-light source.

According to a further embodiment of the present invention the UV-light source(s) is/are arranged in the one or several indentations in such a way that all UV-light sources are located at least partially, potentially even completely inside the outside tube wall (in the case of a tube not having a round cross section), for example inside the outside radius of the tube (in the case of a round tube cross section) of the transparent glass tube, whereby the outside tube wall or respectively the outside tube radius are to be understood as if the indentations were not present.

Even further the indentations may be provided inside the inside tube wall (in the case of a tube cross section which is not round), such as inside the inside tube radius (in the case of a round tube cross section) of the UV-transparent glass tube, whereby the inside tube wall or respectively the inside tube radius are to be understood as if the indentations were not present. Further according to the present invention, arrangements are provided wherein the UV-light sources are located within the inside tube wall or respectively within the tube inside radius, as previously defined, so that an especially favorable radiation distribution is achieved whereby only a small portion of the UV radiation does not reach on a direct path through the glass tube into the interspace of the tube.

In contrast to recesses—as are provided regularly in the current state of the art—for which normally a greater wall thickness in the tube material has to be provided in order to accommodate the UV-light sources, considerably lower wall thicknesses can be utilized in the indentations according to the present invention, so that the light has only to travel a short path through the glass and is not absorbed already to a great extent by the tube material.

If applicable, one or more recesses may be present in addition to the inventive indentations in which, however no UV-light sources may be accommodated, but which have other functions. A recess may for example accommodate a sensor.

According to an additional embodiment, only indentations may be provided in the glass tube. Recesses would then not be present.

The geometry according to the present invention causes the UV-light sources to be closer to the medium to be disinfected, meaning that they are moved in the direction toward the interior space of the tube, resulting in a high portion of UV-radiation directly reaching the medium prior to being reflected. Due to the geometry provided by the present invention a more homogeneous light distribution is achieved in the interior space of the tube, thus increasing the disinfecting efficiency. The result therefore is a higher overall efficiency of the system. The inventive arrangement moreover provides a greater compactness of the system.

A great advantage is also that the device according to the present invention represents a closed system, which operates without external influence. While the medium, for example water, to be disinfected flows through the UV-transparent glass tube, radiation occurs without having to add any additives to the medium. The UV-light sources are possibly also surrounded by the medium without coming into direct contact with the medium. This provides closest proximity to the medium; however the UV-light sources are protected at the same time from the medium by glass sheathing.

Due to the special requirements of the device according to the present invention, the glass tube together with the UV-light sources which are arranged at least partially in the glass wall, and possibly with one or several reflectors can be accommodated for example in a compact housing. The device can be utilized without problem in larger units—for example with flowing medium—such as in a conduit system, or also with stationary medium, for example in a tank or similar equipment. The device may be stationary or permanently installed as part of a larger system or may be flexibly manageable as a hand held device. The actual disinfecting device is hereby composed of a UV-transparent glass tube containing UV-light sources arranged in indentations progressing, for example parallel to the tube axis and, for example one or more reflectors.

Moreover the production of specially formed UV-transparent glass tubes which are utilized in the inventive device can easily be facilitated.

Accordingly, the present invention therefore provides for the utilization of the special glass tube shape with indentations. Very high disinfection efficiency is achieved due to the inventively possible special radiation geometry. The device according to the present invention hereby achieves the highest degree of efficiency possible at relatively low cost expenditure during production.

The device according to the present invention is also suitable for very specialized requirements. For example for the production of ultrapure water which is required in particular in the pharmaceutical, cosmetic and semi-conductor industry fields.

The device shows its advantages in particular in smaller highly compact systems, for example with pressures in the domestic field. The device according to the present invention clearly increases the degree of efficiency compared to known applications.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

Figure 1:
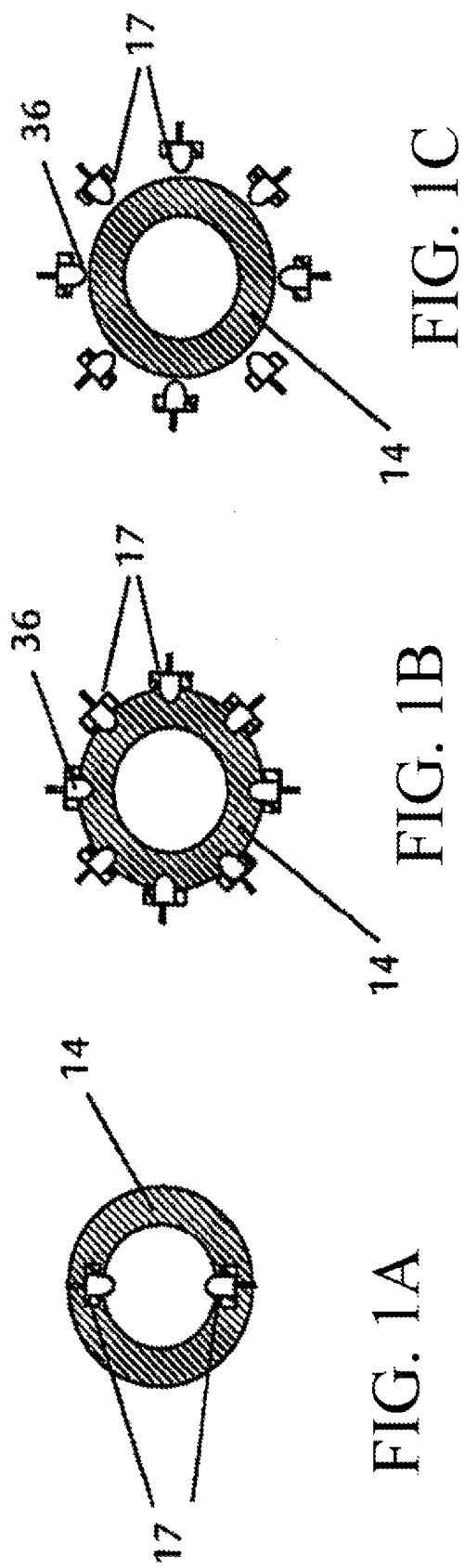
FIGS. 1a, b and c are schematic cross sectional views of exemplary design forms from the current state of the art according to DE 10 2010 005 893 A1 (FIGS. 6b, 6c and 6d of said documentation)

The various elements illustrated in the drawings are only representative and are not necessarily drawn to scale. Certain sections may be exaggerated, whereas others may be minimized. The drawings are intended to illustrate embodiments of the disclosure which can be understood and appropriately implemented by an expert from the state of the art. The same reference numbers and symbols are used in the drawings for like components and elements.

DETAILED DESCRIPTION OF THE INVENTION

Referring now to the drawings, and more particularly to FIGS. 1a, 1b and 1c, there is shown in each a schematic cross sectional view of exemplary embodiments from the current state of the art according to DE 10 2010 005 893 A1 (FIGS. 6b, 6c and 6d of said documentation). FIG. 1a depicts a UV-radiation unit which shows UV-radiation unit 17 integrated into the wall of conduit system 14. UV-radiation devices 17 respectively protrude with their tip area into the tube interior. The light sources are therefore in direct contact with the medium flowing in the interior space and must be permanently sealed against same. A simple replacement is no longer easily possible. The system must be shut down for this purpose.

FIG. 1b illustrates a multitude of UV-radiation devices 17 in the embodiment of UV-LEDs 36 which are integrated into the wall of conduit system 14. UV-LEDs 36 are therefore located in recesses of the tube wall. The illustrated recesses from the current state of the art demonstrate that there is regularly a stronger wall thickness in the tubing material in order to accommodate the UV-light sources. This results in an extension of the path the UV-light must travel through the tube to the medium, thereby generating losses. Moreover, a greater portion of the light emitted from the UV-light source will exit the tube toward the outside or will be directed in the tube wall and is therefore not usable for disinfecting. This geometry is therefore not very suitable for non-directed light sources.

FIG. 1c shows again a multitude of UV-LEDs arranged outside conduit system 14, so that the entire wall thickness of the tube between the UV-light sources and the medium to be disinfected is in place. Losses of UV-light due to residual absorption are therefore inevitable.

Analogous to FIG. 1b this arrangement is also not very suitable for undirected light sources. An additional disadvantage of this arrangement is the large space requirement wherein a multitude of UV-light sources must be arranged around the tube in order to guarantee sufficient disinfection. Such systems are not compact, but instead require a lot of space.

Figure 2:
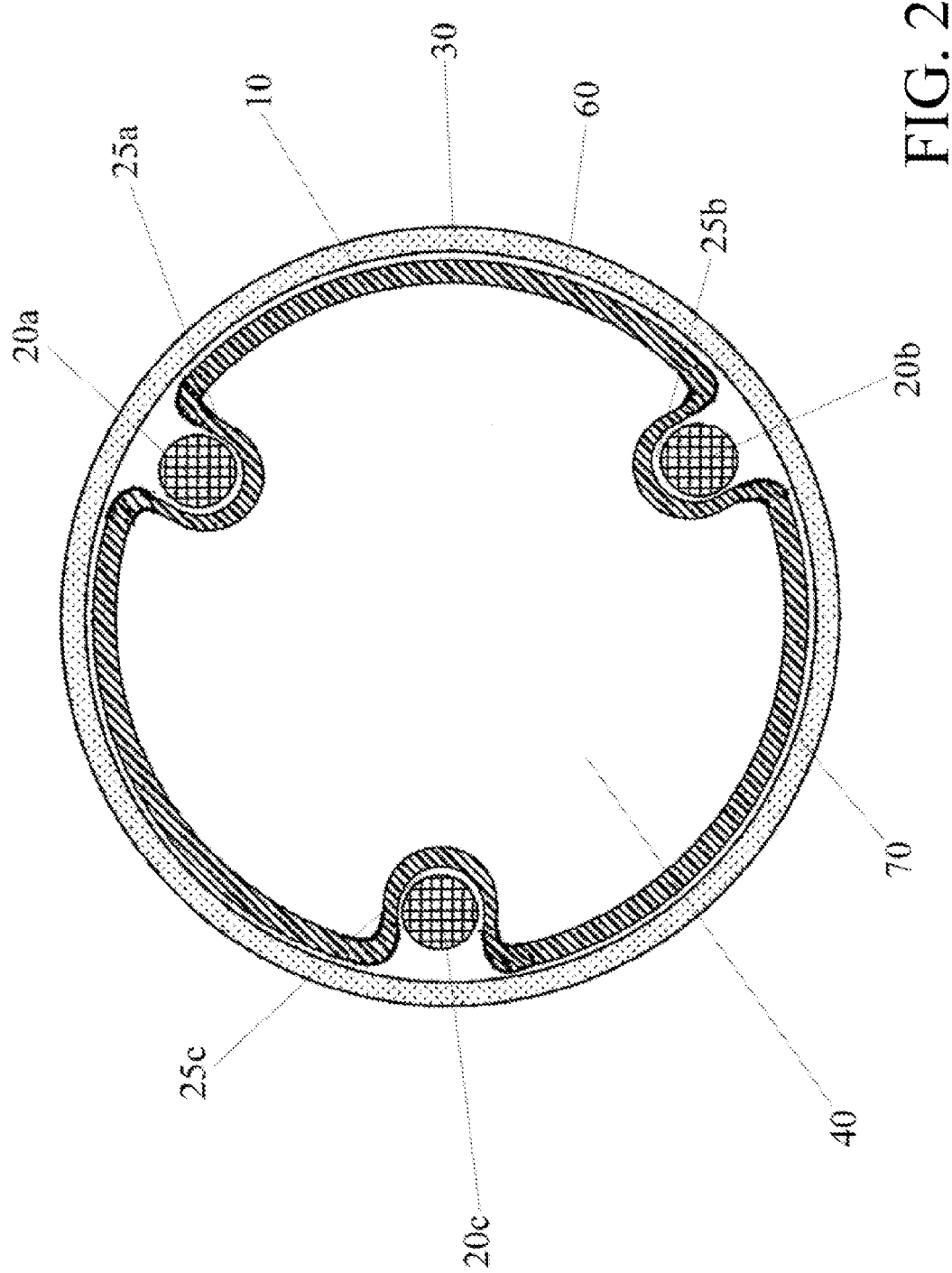
FIG. 2 is a schematic cross sectional view of an embodiment of the present invention having a round UV-transparent glass tube with 3 UV-light sources which are respectively located in an indentation, and a reflector, whereby a reflector is provided around the glass tube and the UV-light sources.

Referring now to FIG. 2, there is shown a schematic cross sectional view of an exemplary embodiment of the present invention having tube 10 with 3 UV light sources 20a, 20b and 20c and one reflector 30. The embodiment depicted in FIG. 2 displays tube-like interior space 40 through which a liquid and/or a gas flows perpendicularly. Tube 10 is constructed of a UV-transparent glass. Any desired glass may be selected, insofar as it is suitable for the application purpose. Tube wall 3 is supplied with indentations 25a, 25b and 25c.

In contrast to the design variations with recesses from the current state of the art in accordance with FIGS. 1a, 1b and 1c, FIG. 2 illustrated indentations according to the current invention. Here, as a rule there is a difference in regard to the wall thickness of glass tube 10 since, in the provision of recesses a greater wall thickness is appropriately provided in order to accommodate the UV-light sources, than is necessary when providing indentations.

In order to obtain an indentation, outside tube wall 60 and inside tube wall 70 are inverted simultaneously toward the inside at the same location, so that indentations 25a, 25b and 25c extend into interior space 40. Indentations 24a, 25b and 25c respectively form hollow spaces or depressions in which UV-light sources 20a, 20b and 20c respectively are arranged and which may be arranged parallel to the direction of flow of the medium to be disinfected. In the current example UV-light sources 20a, 20b and 20c are accommodated completely in the illustrated indentations 25a, 25b and 25c and are situated practically completely within inside tube wall 70—in the illustrated case inside the tube inside radius—if tube 10 were constructed so that there were no indentations. In the illustrated example the number of UV-light sources 20a, 20b and 20c coincides with the number of indentations 25a, 25b and 25c so that one UV-light source 20a, 20b and 20c is provided in each indentation 25a, 25b and 25c respectively. Additional indentations may, for example, also be provided, or more than one UV-light source, for example a bundle of UV-light sources, may be present in one indentation.

Moreover, indentations 25a, 25b and 25c illustrated in FIG. 2 are adapted to the shape of the UV-light sources 20a, 20b and 20c, so that these are completely accommodated in the formed hollow space and no longer protrude toward the outside.

UV-light sources 20a, 20b and 20c illustrated in FIG. 2 are arranged symmetrically in round glass tube 10 which means that they form an equilateral triangle with UV-light sources 20a, 20b and 20c located respectively at the corners of the triangle. Thanks to the inward pointing indentations 25a, 25b and 25c the UV-light takes a shorter path through the tube wall in order to reach interior space 40 where the medium to be disinfected is located. This allows for a great portion of the UV-light to take a direct path through the tube wall to reach interior space 40 where the medium to be disinfected is located. This geometry is advantageous for obtaining an advantageously homogeneous radiation with high radiation density whereby a radiation intensity minimum which normally occurs between the individual UV-light sources can be avoided to a large extent. Other tube cross sections and geometries with another number of indentations and another number of UV-light sources than those shown are also possible.

In addition to indentations 25a, 25b and 25c one or more recesses (not illustrated) can also be provided in glass tube 10 of FIG. 2. These would, for example, not contain a UV-light source, but instead a sensor.

In addition, reflector 30 is provided in FIG. 2 in order to reflect the UV-light which was radiated to the outside back into tube 10. The type, shape, size and structure of reflector 30 are not restricted further according to the present invention. A reflector may be any type of coated surface for the reflection of light, such as a reflective film, a mirror or similar object. Reflector 30 in the current example is arranged positioned around the entire arrangement. Reflector 30 has a round shape and fits closely against outside tube wall 60. Since the three indentations 25a, 25b and 25c are designed such that the three UV-light sources 20a, 20b and 20c contained therein are situated completely in indentations 25a, 25b and 25c and are therefore accommodated offset in the direction of interior space 40 of tube 10 and do no longer protrude to the outside, reflector 30 can be applied directly onto outside tube wall 60. The shown arrangement permits especially simple reflector geometry—reflector 30 is positioned directly on tube 10 and is held and stabilized by it. The reflector can also be attached or applied directly to tube 10. In the current embodiment of the present invention a particularly simple arrangement of the inventive device is achieved, since the device can be totally enclosed by a tube which, at the same time serves as reflector and which is positioned directly on tube 10. Reflector 30 can also be in the embodiment of a UV-reflective coating which is applied directly onto tube 10, for example through vapor deposit.

Figure 3:
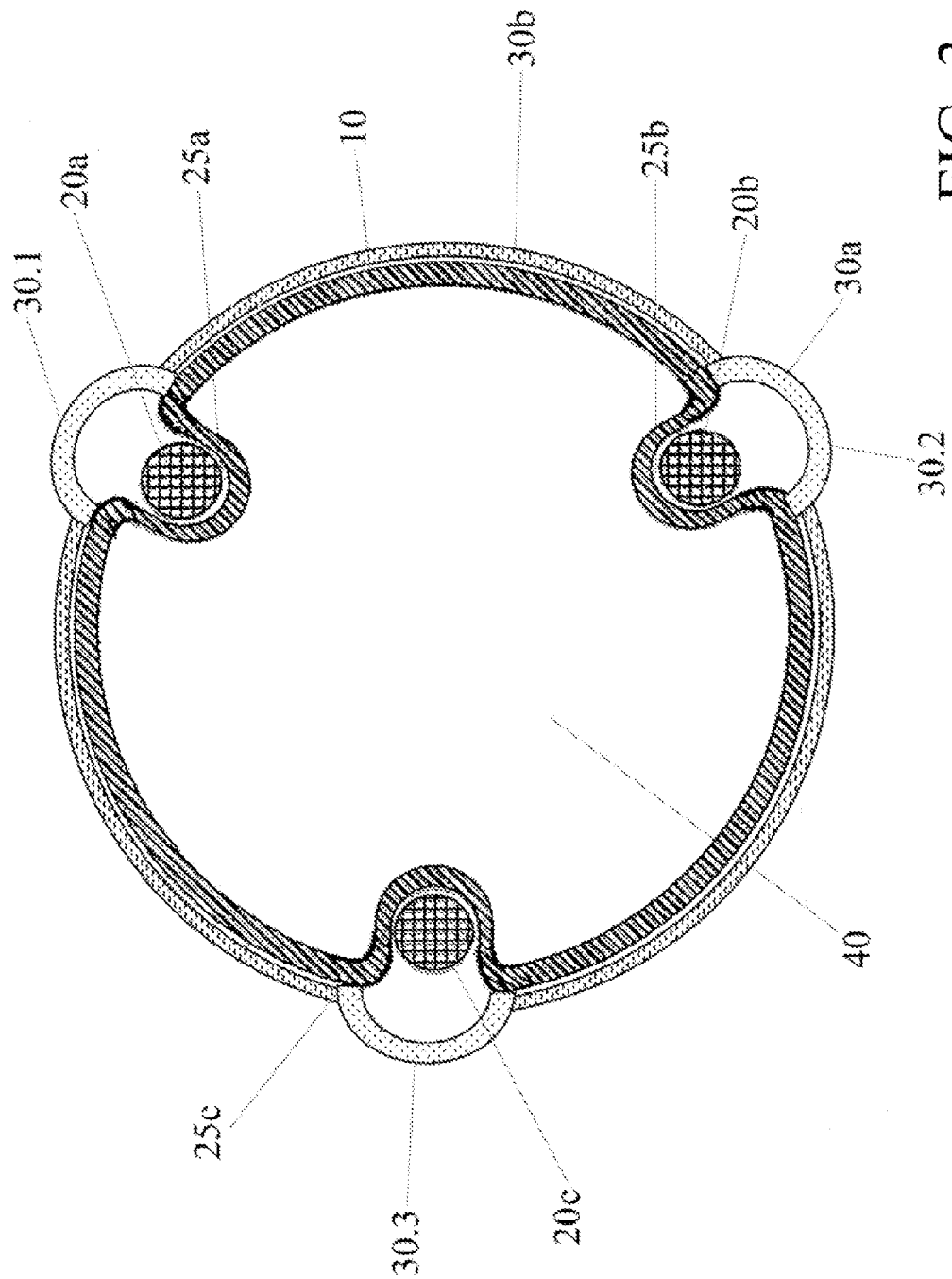
FIG. 3 is a schematic cross sectional view of an additional embodiment of the present invention having a round UV-transparent glass tube with 3 UV-light sources, whereby the tube has a reflector on the outside and whereby in addition a reflector is allocated to each UV-light source.

Referring now to FIG. 3, there is shown a schematic cross sectional view of an additional embodiment of the present invention of a tube 10 with three UV-light sources 20a, 20b and 20c and reflectors 30a and 30b. The embodiment is similar to that shown in FIG. 2, but in addition reflector 30a (30.1, 30.2, 30.3) is allocated to each UV-light source 20a, 20b and 20c respectively.

The shape, size and structure of individual reflectors 30a (30.1, 30.2 and 30.3) allocated to respective UV-light sources 20a, 20b and 20c are freely selectable. In the illustrated example reflectors 30.1, 30.2 and 30.3 are in the form of a spherical sector. The three illustrated reflectors 30.1, 30.2 and 30.3 are all produced to the same size and shape. However, this is not necessary in each instance. Other reflector sizes and designs are also feasible which could be different for each UV-light source 20a, 20b and 20c.

In addition to reflectors 30a (30.1, 30.2 and 30.3) which are arranged around three UV-light sources 20a, 20b and 20c, a further reflector 30b is arranged around tube 10 itself. The illustrated arrangement shows reflector 30b which is placed directly around tube 10 and which is retained and stabilized by same. The reflector may also be fixed directly to tube 10 or may be applied in the form of a UV-reflective coating onto tube 10.

Due to UV-light sources 20a, 20b and 20c which are present in indentations 25a, 25b and 25c and which are arranged such that they are located within tube inside wall 60 (without indentations), the UV-light takes a shorter path to interior space 40 where the medium to be disinfected is located. The portion of the UV-light which is initially reflected by a reflector before it reaches the interior space is clearly reduced, a low-loss transfer of the UV-light results, thus providing better exploitation of the UV-radiation.

Figure 4:
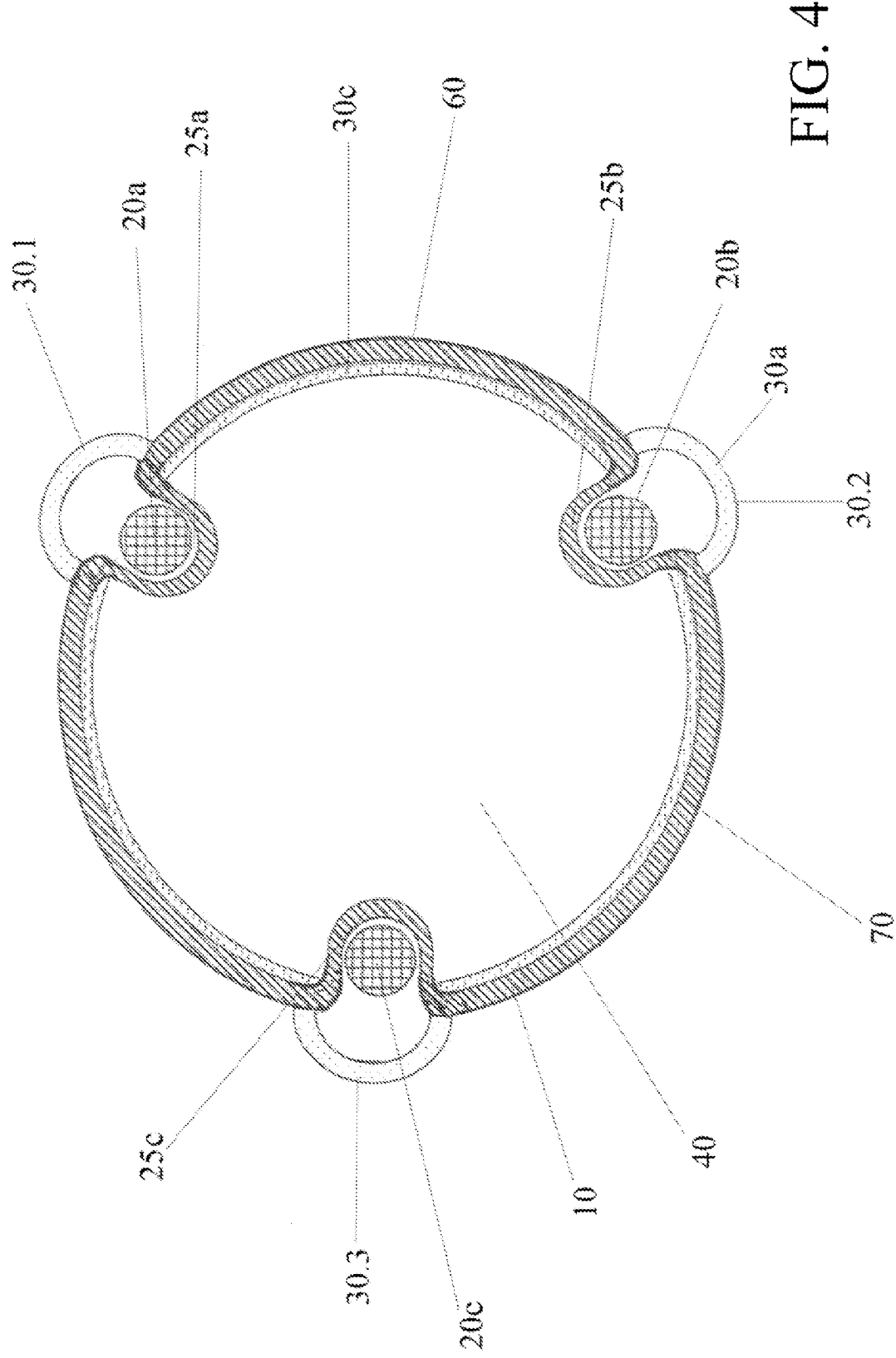
FIG. 4 is a schematic cross sectional view of an additional embodiment of the present invention having a round UV-transparent glass tube with 3 UV-light sources whereby the tube has a reflector on the inside and whereby in addition a reflector is allocated on the outside to each UV-light source.

Referring now to FIG. 4, which is similar to FIG. 3, there is shown a schematic cross sectional view of another embodiment according to the present invention of a round UV-transparent glass tube with three UV-light sources, whereby the tube has a reflector on the inside and whereby in addition a reflector is allocated to each UV-light source. In the area of indentations 25a, 25b and 25c, the inside reflector is of course recessed. The explanations above in reference to FIG. 3 apply accordingly.

Figure 5A:
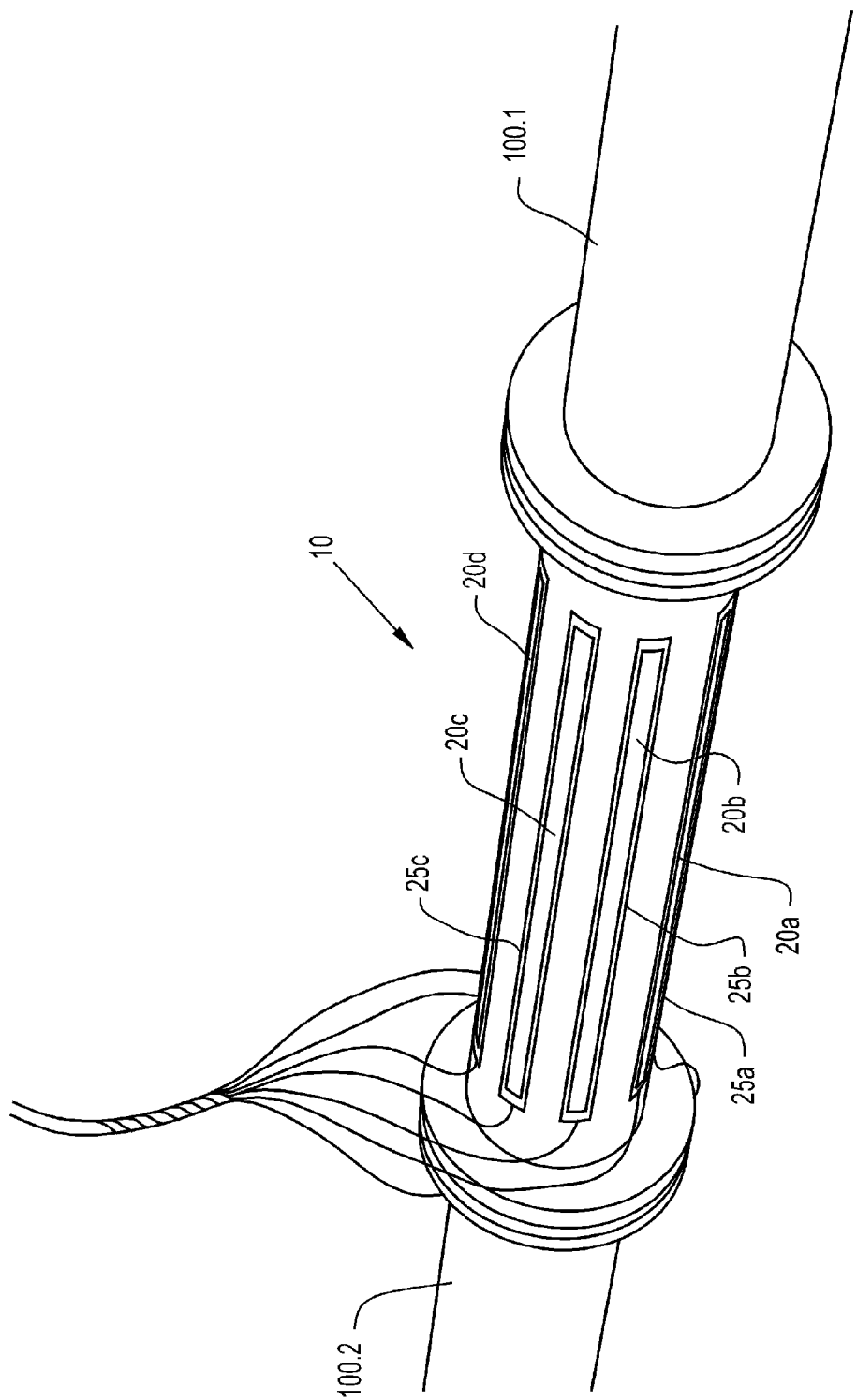
FIG. 5a is a three-dimensional schematic view of an embodiment of a device according to the present invention.
Figure 5B:
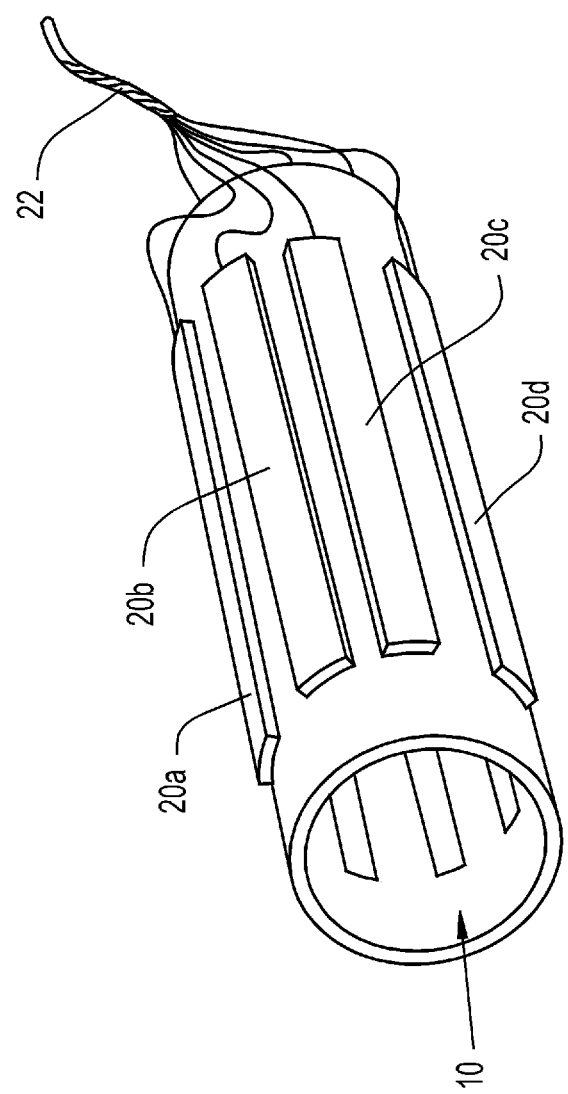
FIG. 5b is a three-dimensional schematic view of an embodiment of a UV-transparent glass tube with several UV-light sources according to the present invention.

Referring now to FIG. 5a, there is illustrated a three-dimensional schematic view of an embodiment of a device in accordance with the present invention. Tube 10 is installed in a conduit system, for example installed between metal pipes 100.1 and 100.2. Tube 10 consists of UV-transparent glass and features indentations 25a, 25b, 25c . . . , in which UV-light sources 20a, 20b, 20c . . . are located. A three-dimensional view of tube 10 from FIG. 5a is shown in FIG. 5b with several UV-light sources, which are connected via connectors 22 with a power source.

Figure 6:
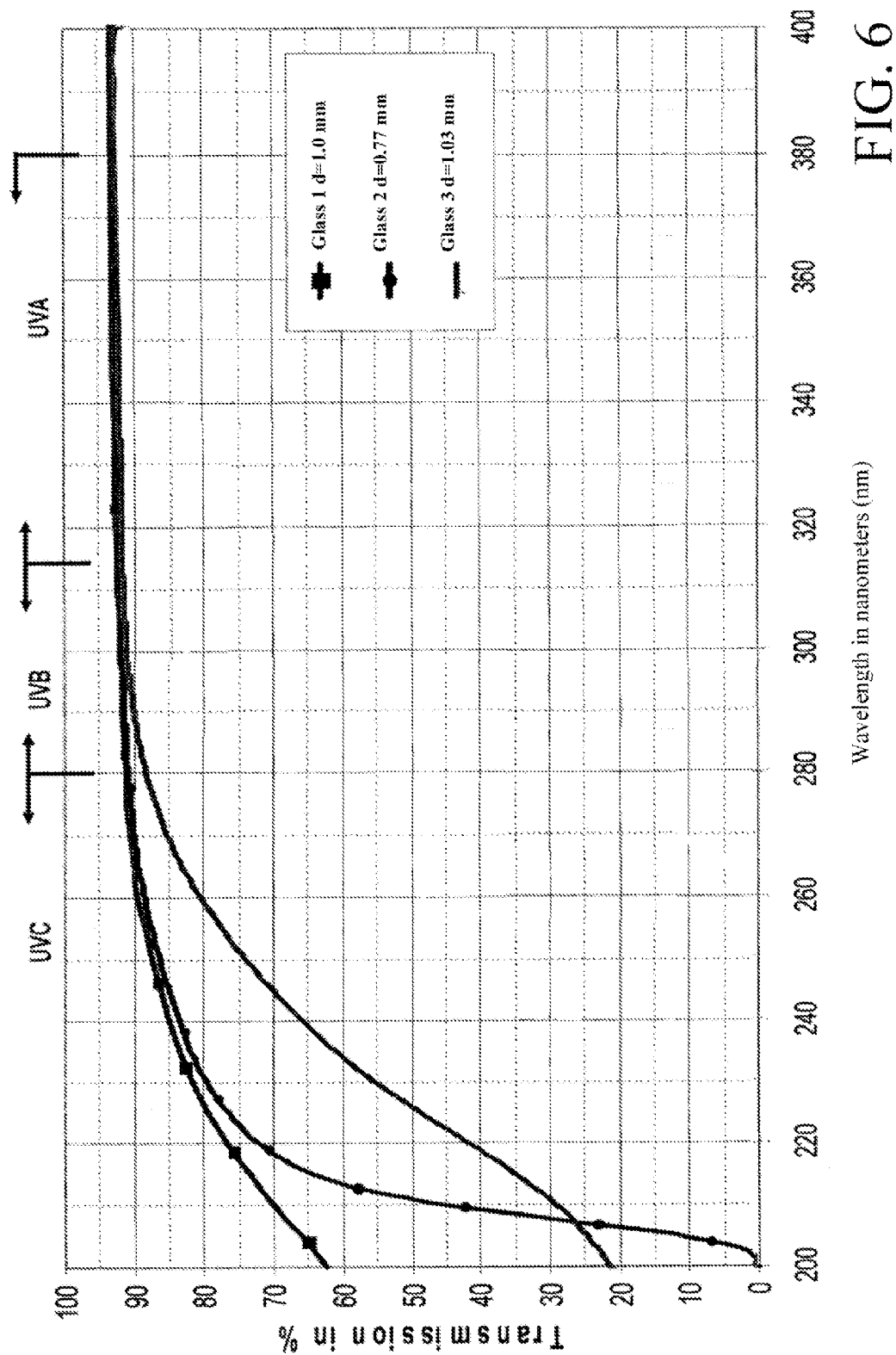
FIG. 6 is a graphic depiction wherein the transmission is plotted against the wavelength (transmission progression) for 3 UV-transparent glasses according to the present invention.

The UV-transparent glass is not particularly restricted. The transmission progression for UV-transparent glasses is shown in FIG. 6 in the form of a graphic depiction. The transmission (in %) is here plotted against the wavelength (in nm) for several UV-transparent glasses. FIG. 6 indicates the UV-transmission for Glass 1, glass 2 and glass 3.

FIGS. 1 to 6 clarify are merely exemplary arrangements. The invention is not limited to these and they represent merely examples of possible design variations. Other possibilities are also feasible.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

COMPONENT IDENTIFICATION LISTING

10 Glass tube
14 Conduit system from the current state of the art

17 UV-radiation device from the current state of the art
20a, 20b, 20c . . . UV-light source
25a, 25b, 25c . . . Indentation
22 Connections
30, 30a, 30b, 30.1, 30.2, 30.3 . . . Reflector
36 UV-LEDs from the current state of the art
40 Interior tube space
60 Outside tube wall
70 Inside tube wall
100.1, 100.2 Metal pipe

What is claimed is:

1. A device for disinfecting at least one of gases and liquids, the device comprising:
 a tube formed of an ultraviolet (UV)-transparent glass and having a hollow interior space defining a fluid flow path and a tube wall including a tube inside wall and a tube outside wall, said UV-transparent glass tube defining a tube axis and having an indentation extending into said hollow interior space on at least one location, said indentation progressing generally parallel to said tube axis; and
 a UV-light source arranged in said indentation.

2. The device according to claim 1, wherein said outside tube wall does not include said indentation and said UV-light source is positioned at least partially within said outside tube wall of said UV-transparent glass tube.

3. The device according to claim 2, wherein said UV-light source is positioned completely within said outside tube wall of said UV-transparent glass tube.

4. The device according to claim 1, wherein said UV-light source is one UV-light source of a predetermined number of UV-light sources and said indentation is one indentation of a predetermined number of indentations corresponding with said predetermined number of UV-light sources.

5. The device according to claim 4, wherein only one of said predetermined number of UV-light sources is provided in a corresponding one of said predetermined number of indentations.

6. The device according to claim 4, wherein said predetermined number of UV-light sources provided in said UV-transparent glass tube is between 1 and 8 and only one of a single of said predetermined number of UV-light sources and a group of said predetermined number of UV-light sources is provided in a corresponding one of said predetermined number of indentations.

7. The device according to claim 6, wherein said predetermined number of UV-light sources provided in said UV-transparent glass tube is between 1 and 6.

8. The device according to claim 7, wherein said predetermined number of UV-light sources provided in said UV-transparent glass tube is between 1 and 5.

9. The device according to claim 8, wherein said predetermined number of UV-light sources provided in said UV-transparent glass tube is between 1 and 4.

10. The device according to claim 9, wherein said predetermined number of UV-light sources provided in said UV-transparent glass tube is between 1 and 3.

11. The device according to claim 1, wherein said UV-transparent glass forming said tube is selected from one of a quartz glass and a silicate glass.

12. The device according to claim 11, wherein said silicate glass is one of a borosilicate glass and a sodium-potassium-barium-silicate glass.

13. The device according to claim 1, wherein said UV-transparent glass forming said tube has a composition including:

| | | |
|---|---|---|
| $SiO_2$ | 75-85 | weight percent (wt. %); |
| $B_2O_3$ | 8-15 | wt. %; |
| $Al_2O_3$ | 0.5-4 | wt. %; |
| $Na_2O$ | 1-6 | wt. %; |
| $K_2O$ | 0.1-2 | wt. %; |
| $ZrO_2$ | <0.005 | wt. %; | a content of $Fe_2O_3$ which is one of <100 parts per million (ppm) and <10 ppm;
a content of $TiO_2$ which is one of <100 ppm and <10 ppm; and
a content of a fining agent.

14. The device according to claim 1, wherein said UV-transparent glass forming said tube has a composition including:

| | | |
|---|---|---|
| $SiO_2$ | 65-75 | weight percent (wt. %); |
| $B_2O_3$ | 15-22 | wt. %; |
| $Al_2O_3$ | 4.5-7 | wt. %; |
| $Na_2O$ | 1.5-4 | wt. %; |
| $K_2O$ | 0.5-3 | wt. %; |
| $Li_2O$ | 0.1-1.5 | wt. %; |
| BaO | 0.5-4 | wt. %; |
| CaO | 0.1-2 | wt. %; |
| MgO | <0.01 | wt. %; | a content of $Fe_2O_3$ which is one of <100 parts per million (ppm) and <10 ppm;
a content of $TiO_2$ which is one of <100 ppm and <10 ppm; and
a content of a fining agent.

15. The device according to claim 1, wherein said UV-transparent glass forming said tube has a composition including:

| | | |
|---|---|---|
| $SiO_2$ | 65-78 | weight percent (wt. %); |
| $B_2O_3$ | 0.5-4 | wt. %; |
| $Al_2O_3$ | 0.5-4 | wt. %; |
| $Na_2O$ | 5-10 | wt. %; |
| $K_2O$ | 8-14 | wt. %; |
| BaO | 5-8 | wt. %; | a content of $Fe_2O_3$ which is one of <100 parts per million (ppm) and <10 ppm;
a content of $TiO_2$ which is one of <100 ppm and <10 ppm;
a content of CaO which is one of <100 ppm and <10 ppm;
a content of MgO which is one of <100 ppm and <10 ppm; and
a content of a fining agent.

16. The device according to claim 1, further comprising a reflector which is one of:
 a) arranged around and completely encasing said tube;
 b) mounted on or applied to said outside tube wall and said reflector is not provided in an area of said indentation;
 c) mounted on or applied to said inside tube wall and said reflector is not provided in an area of said indentation;
 d) arranged around said glass tube, mounted on or applied to said outside tube wall except in an area of said indentation, wherein an additional reflector is provided for said UV-light source; and
 e) mounted on or applied to said inside tube wall except in an area of said indentation, wherein an additional reflector is provided for said light UV-light source.

17. The device according to claim 16, wherein said reflector applied to one of said outside tube wall and said inside tube wall is in the form of a UV-reflective coating except in said area of said indentation.

18. The device according to claim 1, wherein said UV-light source is one of a medium pressure UV-lamp, a high pressure UV-lamp, a low pressure UV-lamp, a UV-light emitting diode (LED) and a cold cathode light (CCL).

19. The device according to claim 18, wherein said low pressure UV-lamp is a mercury low pressure lamp.

20. The device according to claim 4, wherein said predetermined number of indentations are locally limited in said UV-transparent glass tube.

21. The device according to claim 1, wherein a shape of said indentation is adapted to a corresponding shape of said UV-light source.

22. The device according to claim 1, wherein a wall thickness of said UV-transparent glass tube is constant along a tube circumference when providing said indentation.

23. The device according to claim 1, wherein a cross section of said UV-transparent glass tube is one of round, oval and angular.

24. The device according to claim 23, wherein said angular shape of said UV-transparent glass tube has one of 3, 4, 5, 6, 7 and 8 corners.

25. The device according to claim 1, said UV-transparent glass tube further including at least one recess in addition to said indentation, wherein no UV-light sources are positioned in said at least one recess.

26. The device according to claim 4, wherein said predetermined number of UV-light sources are arranged symmetrically.

27. The device according to claim 26, wherein said predetermined number of UV-light sources are in an arrangement which is one of axially symmetric, mirror symmetric, rotationally symmetric and centrically symmetric.

28. A method for disinfecting at least one of a liquid and a gas, the method comprising the steps of:
providing a tube formed of an ultraviolet (UV)-transparent glass and having a hollow interior space defining a fluid flow path and a tube wall including a tube inside wall and a tube outside wall, said UV-transparent glass tube defining a tube axis and having an indentation extending into said hollow interior space on at least one location, said indentation progressing generally parallel to said tube axis;
providing a UV-light source arranged in said at least one indentation; and
using said tube and said UV-light source arranged in said indentation of said tube to disinfect at least one of a liquid and a gas in one of a stationary and a flowing condition.

* * * * *